US008655435B2

(12) United States Patent
Hwang et al.

(10) Patent No.: US 8,655,435 B2
(45) Date of Patent: Feb. 18, 2014

(54) APPARATUS AND METHOD FOR GENERATING ATRIAL FIBRILLATION PREDICTION MODEL, AND APPARATUS AND METHOD FOR PREDICTING ATRIAL FIBRILLATION

(75) Inventors: Heasoo Hwang, Seoul (KR); Hyoa Kang, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/561,403

(22) Filed: Jul. 30, 2012

(65) Prior Publication Data

US 2013/0204149 A1 Aug. 8, 2013

(30) Foreign Application Priority Data

Feb. 8, 2012 (KR) ........................ 10-2012-0012960

(51) Int. Cl.
*A61B 5/04* (2006.01)

(52) U.S. Cl.
USPC .......................................................... 600/518

(58) Field of Classification Search
USPC .......................................................... 600/518
See application file for complete search history.

(56) References Cited

U.S. PATENT DOCUMENTS 7,996,073 B2 8/2011 Busche et al.
8,014,852 B2 9/2011 Kwek et al.
2008/0167567 A1 7/2008 Bashour et al.
2010/0094274 A1 4/2010 Narayan et al.
2010/0217144 A1 * 8/2010 Brian ........................... 600/523

FOREIGN PATENT DOCUMENTS

KR 10-1998-0030894 7/1998
KR 10-2003-0069586 8/2003
KR 10-2010-0111234 10/2010
KR 10-2011-0082038 7/2011

OTHER PUBLICATIONS

Poli, et al. "Prediction of Atrial Fibrillation from Surface ECG: Review of Methods and Algorithms," Ann. 1st. Super Sanita 39(2) 195-203, 2003 (9 pages, in English).

Syed, et al. "Motif Discovery in Physiological Datasets: A Methodology for Inferring Predictive Elements," ACM Transactions on Knowledge Discovery from Data vol. 4 No. 1, Jan. 2010 (29 pages, in English).

Lee et al. The Role of P Wave from Surface Electrocardiography for the Prediction of Atrial Fibrillation after Coronary Artery Bypass Graft Surgery, Korean Circulation J 2005, 35:677-682 (6 pages, including English language abstract).

* cited by examiner

*Primary Examiner* — George Manuel
(74) *Attorney, Agent, or Firm* — NSIP Law

(57) ABSTRACT

An apparatus and a method to generate an atrial fibrillation prediction model, and an apparatus and a method to predict atrial fibrillation are provided. An atrial fibrillation (AF) prediction model generating apparatus includes a feature extractor configured to extract T-wave features in a predetermined time period from electrocardiogram data and generate a T-wave feature profile based on the extracted features, and a prediction model generator configured to classify the generated T-wave feature profile and generate an AF prediction model using the classified feature profile.

22 Claims, 6 Drawing Sheets

100
ELECTROCARDIOGRAM DB
130
NOISE REMOVER
111
T-WAVE DETECTOR
112
FEATURE GENERATOR
113
PROFILE GENERATOR
114
110
PREDICTION MODEL GENERATOR
120
PREDICTION MODEL DB
140

APPARATUS AND METHOD FOR GENERATING ATRIAL FIBRILLATION PREDICTION MODEL, AND APPARATUS AND METHOD FOR PREDICTING ATRIAL FIBRILLATION

CROSS-REFERENCE TO RELATED APPLICATIONS

This application claims the benefit under 35 U.S.C. §119 (a) of Korean Patent Application No. 10-2012-0012960, filed on Feb. 8, 2012, the entire disclosure of which is incorporated herein by reference for all purposes.

BACKGROUND

1. Field

The following description relates to atrial fibrillation (AF) prediction, such as, for example, technology to generate an AF prediction model and predicting AF based on information about a T wave.

2. Description of Related Art

Arrhythmia is a state in which a beat is too slow, too fast, or irregular. Arrhythmia occurs due to an abnormal rate of muscle contractions in the heart. AF is a symptom of arrhythmia. AF represents a state in which an atrium of a heart does not beat at a normal rhythm. AF may cause some parts of the atrium to experience minute trembles at an irregular rate such that fast and irregular heartbeats occur as a result.

AF may itself cause symptoms such as dyspnea, chest pain, and the like. As the occurrence of AF increases, there is a possibility that arrhythmia will occur that is of greater seriousness and danger. For example, AF may eventually hamper the effective pumping of blood out of the heart. As such, AF patients have a stroke risk that five times greater than a stroke risk of those without AF. In addition, AF patients have death rate that is two times greater than a death rate of those without AF Further, AF is an arrhythmia symptom that is relatively commonly diagnosed among patients suffering from arrhythmia. AF is the most common of the arrhythmia symptoms, typically resulting in 33% of all arrhythmia-related inpatient hospital stays. Accordingly, a technique to accurately predict the generation of AF at an early stage is desired by those practicing in the medical field.

If a sudden generation of AF causes a heartbeat to increase to a rate that is too fast, blood is not able to be filled in the heart within a sufficient time period. As a result, cardiac output, which is a total amount of blood pumped out of a heart upon contraction of the heart, is sharply reduced. Since a contraction of an atrium of a normal heart occupies about 30% of cardiac output, the heart rate continues to increase to fill the insufficient cardiac output.

Accordingly, the exceedingly fast beating of the heart causes an overload, which results in a deterioration in heart function to the point that that heart begins to experience structural changes. This may lead to heart failure or cause a heart that is already in a state of failure to worsen in condition. Moreover, if the heart fails contract normally as a result of AF, blood congestion may occur in the heart, thereby increasing a risk of blood coagulation in the heart.

As a result, blood clots formed in the heart move out through arteries, thereby serving to block blood vessels in the brain or other parts of the body. Accordingly, AF patients have a very high risk of stroke or thromboembolism.

Because AF is the most common of complications that occurs after operations such as thoracic surgery, coronary artery bypass grafting (CABG), and the like, accurate prediction of AF in patients that will have or have had operations is very useful in the medical field. Accurate prediction of AF increases a possibility that various cardiac pacing methods can be used to prevent AF, reduce hospital costs, and minimize patient pain.

For example, if an AF risk assessment is performed to accurately estimate a risk of post-operational AF generation in a patient scheduled to have an operation, patients having a high risk of post-operational AF generation can be prescribed appropriate antidysrhythmic treatments, such as drugs, electrical pacing, and the like, to prevent occurrence of AF at an early stage. In addition, patients having a low risk of post-operational AF generation can be freed from being subject to certain protective and preventative care.

SUMMARY

In one general aspect, an atrial fibrillation (AF) prediction model generating apparatus includes a feature extractor configured to extract T-wave features in a predetermined time period from electrocardiogram data and generate a T-wave feature profile based on the extracted T-wave features, and a prediction model generator configured to classify the generated T-wave feature profile and generate an AF prediction model based on the classified feature profile.

The AF prediction model generating apparatus may include that the feature extractor includes a noise remover, a T-wave detector, a derived feature generator, and a profile generator, the noise remover being configured to eliminate noise in the electrocardiogram data, the T-wave detector being configured to detect T-wave basic features in the predetermined time period from the electrocardiogram data from which the noise has been eliminated, the derived feature generator being configured to analyze the detected T-wave basic features and generate T-wave derived features for beats occurring during the predetermined time period based on the analyzed T-wave basic features, the profile generator being configured to generate the T-wave feature profile based on the generated T-wave derived features for the beats occurring during the predetermined time period.

The AF prediction model generating apparatus may include that the profile generator is further configured to calculate mean values of the generated T-wave derived features for the beats occurring during the predetermined time period and generate the T-wave feature profile based on the calculated mean values.

The AF prediction model generating apparatus may include that the profile generator is further configured to calculate mean values of the generated T-wave derived features for the beats occurring during the predetermined time period, select ones of the generated T-wave derived features that are within standard deviations with respect to the calculated mean values, respectively, and generate the T-wave feature profile based on the selected ones of the generated T-wave derived features.

The AF prediction model generating apparatus may include that the profile generator is further configured to compare the generated T-wave derived features for the beats occurring during the predetermined time period to predetermined threshold conditions, select ones of the generated T-wave derived features that meet the predetermined threshold conditions, and generate the T-wave feature profile based on the selected ones of the generated T-wave derived features.

The AF prediction model generating apparatus may include that the T-wave detector is further configured to detect the T-wave basic features in the predetermined time period from the electrocardiogram data for one or more measurement channels.

The AF prediction model generating apparatus may include that the detected T-wave basic features include one or more first pieces of information selected from the group consisting of a T-wave start location, a T-wave peak location, a T-wave termination location, a T-wave amplitude, a T-wave area, a T-wave left area, and a T-wave right area.

The AF prediction model generating apparatus may include that the generated T-wave derived features includes one or more second pieces of information selected from the group consisting of a T-wave duration, a T-wave left duration, a T-wave right duration, a change in the T-wave duration, a change in the T-wave left duration, a change in the T-wave right duration, a change in the T-wave amplitude, a change in the T-wave area, a change in the T-wave left area, and a change in the T-wave right area.

The AF prediction model generating apparatus may include that the prediction model generator is further configured to compare T-wave feature profiles of an AF patient group to T-wave feature profiles of an AF non-patient group, the T-wave feature profiles being generated by the feature extractor, classify AF aspects according to T-wave derived feature patterns included in the T-wave feature profiles, and generate AF prediction models based on the classified AF aspects.

The AF prediction model generating apparatus may include an electrocardiogram database configured to store electrocardiogram data of at least one AF patient and at least one AF non-patient.

The AF prediction model generating apparatus may include a prediction model database configured to store the generated AF prediction model.

In another general aspect, an atrial fibrillation (AF) prediction apparatus includes a feature extractor configured to extract T-wave features in a predetermined time period from electrocardiogram data of a target that is collected in real time and generate a T-wave feature profile based on the extracted T-wave features, an AF predictor configured to search for a T-wave derived feature pattern according to an AF aspect corresponding to the generated T-wave feature profile with reference to AF prediction models and predict a possibility of AF generation in the target as a result, and a prediction result output unit configured to output the predicted result.

The AF prediction apparatus may include that the feature extractor includes a noise remover, a T-wave detector, a derived features generator, and a profile generator, the noise remover being configured to eliminate noise and baseline wandering included in the electrocardiogram data, the T-wave detector being configured to detect T-wave basic features in the predetermined time period from the electrocardiogram data from which the noise has been eliminated, the derived features generator being configured to analyze the detected T-wave basic features and generate T-wave derived features for beats occurring during the predetermined time period based on the analyzed T-wave basic features, the profile generator being configured to generate the T-wave feature profile based on the generated T-wave derived features for the beats occurring during the predetermined time period.

The AF prediction apparatus may include that the profile generator is further configured to calculate mean values of the generated T-wave derived features for the beats occurring during the predetermined time period and generate the T-wave feature profile based on the calculated mean values of the generated T-wave derived features for the beats occurring during the predetermined time period.

The AF prediction apparatus may include that the profile generator is further configured to calculate mean values of the generated T-wave derived features for the beats occurring during the predetermined time period, select ones of the generated T-wave derived features that are within standard deviations with respect to the calculated mean values, respectively, and generate the T-wave feature profile based on the selected ones of the generated T-wave derived features.

The AF prediction apparatus may include that the profile generator is further configured to compare the generated T-wave derived features for the beats occurring during the predetermined time period to predetermined threshold conditions, select ones of the generated T-wave derived features that meet the predetermined threshold conditions, and generate the T-wave feature profile based on the selected ones of the generated T-wave derived features.

The AF prediction apparatus may include that the T-wave detector is further configured to detect the T-wave basic features in the predetermined time period from the electrocardiogram data for one or more measurement channels.

The AF prediction apparatus may include that the detected T-wave basic features include one or more first pieces of information selected from the group consisting of a T-wave start location, a T-wave peak location, a T-wave termination location, a T-wave amplitude, a T-wave area, a T-wave left area, and a T-wave right area.

The AF prediction apparatus may include that the generated T-wave derived features include one or more second pieces of information selected from the group consisting of a T-wave duration, a T-wave left duration, a T-wave right duration, a change in the T-wave duration, a change in the T-wave left duration, a change in the T-wave right duration, a change in the T-wave amplitude, a change in the T-wave area, a change in the T-wave left area, and a change in the T-wave right area.

The AF prediction apparatus may include a prediction model database configured to store ones of the AF prediction models that classify AF aspects according to T-wave derived feature patterns included in T-wave feature profiles.

In yet another general aspect, a method of generating an atrial fibrillation (AF) prediction model includes eliminating noise included in electrocardiogram data, detecting T-wave basic features in a predetermined time period from the electrocardiogram data from which the noise has been eliminated, analyzing the T-wave basic features and generating T-wave derived features for beats occurring during the predetermined time period based on the analyzed T-wave basic features, generating a T-wave feature profile based on the generated T-wave derived features for the beats occurring during the predetermined time period, and classifying the generated T-wave feature profile and generating an AF prediction model based on the classified T-wave feature profile.

In still another general aspect, an atrial fibrillation (AF) prediction method includes eliminating noise from electrocardiogram data of a target, which is collected in real time, detecting T-wave basic features in a predetermined time period from the electrocardiogram data from which the noise has been eliminated, analyzing the detected T-wave basic features and generating T-wave derived features for beats occurring during the predetermined time period based on the analyzed T-wave basic features, generating a T-wave feature profile of the target based on the generated T-wave derived features for the beats occurring during the predetermined time period, predicting an AF generation possibility of the target as a result, the predicting of the result including searching for a T-wave derived feature pattern according to an AF aspect corresponding to the generated T-wave feature profile of the target with reference to pre-stored AF prediction models, and outputting the predicted result regarding the AF generation possibility of the target. Other features and aspects will be apparent from the following detailed description, the drawings, and the claims.

Figure 1:
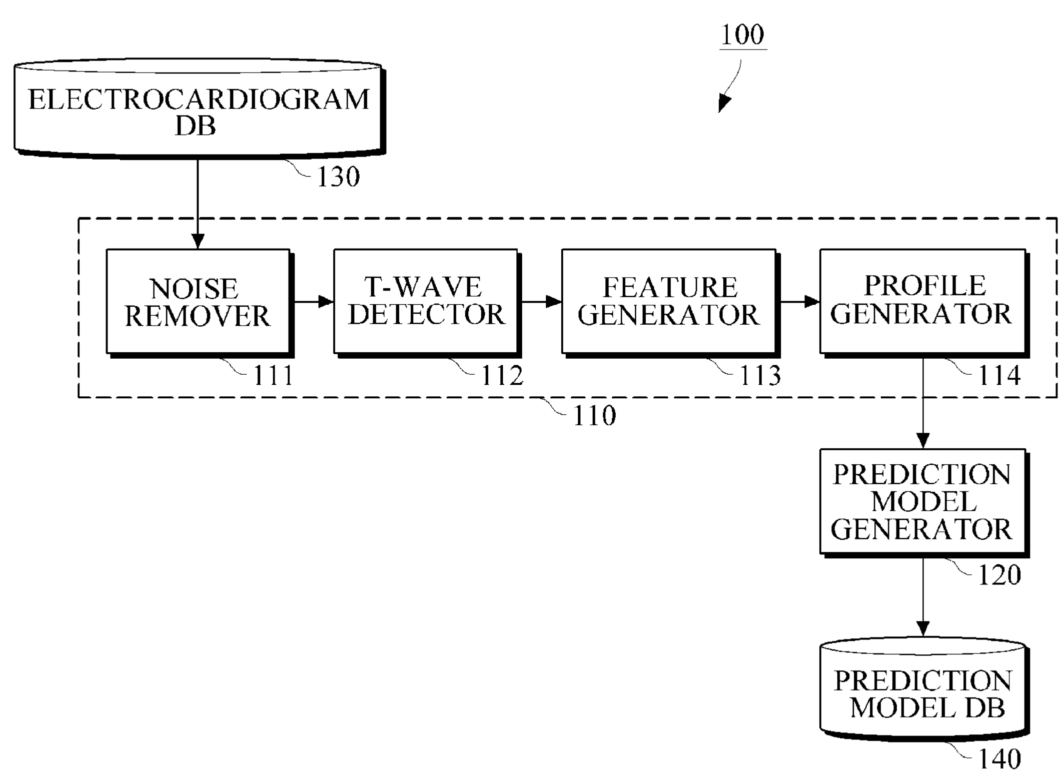
FIG. 1 is a block diagram illustrating an example of an AF prediction model generating apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 is a block diagram illustrating an example of an AF prediction model generating apparatus 100. As illustrated in FIG. 1, the AF prediction model generating apparatus 100 includes a feature extractor 110, a prediction model generator 120, an electrocardiogram database 130, and a prediction model database 140.

The feature extractor 110 extracts the features of a T wave in a predetermined time period from electrocardiogram data and analyzes the features of the T wave to thereby generate a T-wave feature profile. The electrocardiogram data is measured by an electrocardiogram measuring apparatus (not shown). In this example, pieces of electrocardiogram data are measured through a number of measurement channels according to a number of electrodes that are attached to a body.

The myocardium is depolarized sequentially. In other words, the ventricle is depolarized after the atrium is depolarized. While the ventricle is depolarized, the atrium is repolarized. Then, the ventricle is repolarized after the atrium is repolarized.

The depolarization and repolarization of the myocardium occur sequentially, and a potential difference depends on a location of the heart. The phenomenon can be sensed by attaching electrodes onto skin of the body. The electrocardiogram measuring apparatus acquires electrocardiogram data according to an occurrence of the phenomenon.

Figure 2:
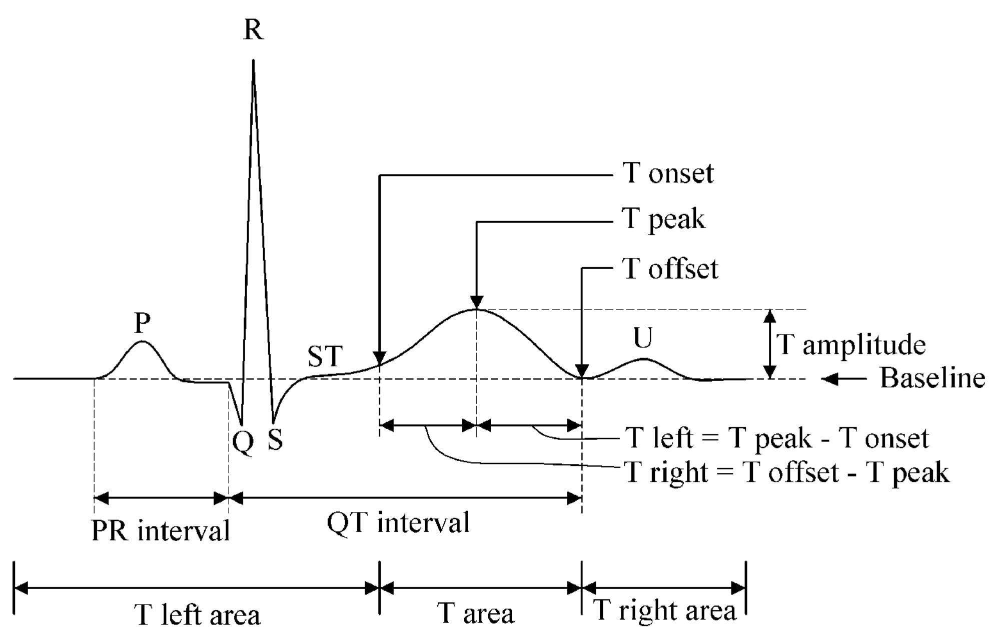
FIG. 2 is a diagram illustrating an example of an electrocardiogram data waveform corresponding to a beat.

FIG. 2 shows an example of an electrocardiogram data waveform corresponding to a beat, where the electrocardiogram data waveform shows a change in intensity of an electrical signal when a heartbeat occurs one time.

An electrocardiogram data waveform in one heartbeat includes a P wave, a QRS wave, a T wave, and a U wave, and also includes factors, such as a PR interval, a QT interval, a ST segment, and the like. The P wave is a signal regarding the depolarization of the atrium, which occurs when an impulse from a sinoatrial node is transferred to the atrium.

The QRS wave includes three waves of Q, R, and S. The QRS wave is a signal regarding the depolarization of the ventricle. Like the atrium, the ventricle is depolarized rapidly because a His-purkinje system is rapider than an atrial conduction system.

The T wave is a signal regarding the repolarization of the ventricle. A height and width of the T wave are not uniform. The U wave is a slow wave that appears at the final stage of the repolarization of the ventricle. The U wave starts either gradually or abruptly from either a baseline or a latter part of the T wave.

The PR interval is a time interval from an initial stage of the depolarization of the atrium to an initial stage of the depolarization of the ventricle. The QT interval is a time interval from the initial stage of the depolarization of the ventricle to a final stage of the repolarization of the ventricle. The ST segment represents the initial repolarization state of the left and right ventricles. The initial repolarization state of the left and right ventricles is the state in which muscles of the ventricle have been depolarized.

Since the ST segment is the state in which the ventricle muscles have been depolarized, if a voltage of the ST segment is not equal to the baseline, the ventricle muscle cells have not been simultaneously depolarized. This is an indication of a chronic phenomenon, such as myocardial infarction.

In order to generate an AF prediction model using the T-wave information, in this example, the feature extractor 110 includes a noise remover 111, a T-wave detector 112, a derived feature generator 113, and a profile generator 114.

The noise remover 111 eliminates noise included in electrocardiogram data. Electrocardiogram data may include noise, baseline wandering, and other factors known to cause inaccurate measurement to the those of ordinary skill in the art. The noise remover 111 serves to eliminate these inaccurate measurement factors.

The T-wave detector 112 detects basic features of the T wave in a predetermined time period from the electrocardiogram data from which noise has been eliminated by the noise remover 111. Here, the predetermined time period extends from a previous time point to a current time point. The example of the electrocardiogram data illustrated in FIG. 2 may appear several times in the predetermined time period since a plurality of heartbeats may occur in the predetermined time period.

Meanwhile, since the electrocardiogram data is measured by an electrocardiogram measuring apparatus (not shown) and, in this example, a plurality of pieces of electrocardiogram data are measured through a plurality of measurement channels according to the number of electrodes attached onto a body, the T-wave detector 112 detects the T-wave basic features in the predetermined time period for each of the measurement channels using the measured electrocardiogram data.

Further, in this example, the basic features of the T wave include, as shown in FIG. 2, one or more pieces of information among a T-wave start location $T_{onset}$, a T-wave peak location $T_{peak}$, a T-wave termination location $T_{offset}$, a T-wave amplitude $T_{amplitude}$, a T-wave area $T_{area}$, a T-wave left area, and a T-wave right area.

The derived feature generator 113 analyzes the T-wave basic features to generate derived features of the T wave for each beat. In this example, the derived features of the T wave, derived from the T-wave basic features, include one or more pieces of information among a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change ($\Delta T_{left}$) in T-wave left duration, a change ($\Delta T_{right}$) in T-wave right duration, a change in T-wave amplitude, a change in T-wave area, a change in T-wave left area, and a change in T-wave right area.

The profile generator 114 generates a T-wave feature profile based on the T-wave derived features for each of the beats. The T-wave feature profile, in this example, includes a T-wave derived feature pattern, and is information that is used to search for an AF prediction model upon AF prediction.

In this example, the profile generator 114 calculates mean values of the generated T-wave derived features for all beats, thereby generating a T-wave feature profile. If three beats occur in a predetermined time period, derived features of three T waves are generated for the three beats by the derived feature generator 113.

The T-wave derived features for each beat may have factors including a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change in T-wave left area, a change in T-wave right area, and other factors known to one having ordinary skill in the art. Accordingly, in this example, the profile generator 114 calculates mean values of factors included in the derived features of the three T waves.

After calculating the mean values of the factors, the profile generator 114 generates a new T-wave derived feature pattern formed with factors having the mean values, and generates a T-wave feature profile including the new T-wave derived feature pattern.

In an example, the profile generator 114 calculates mean values of the T-wave derived features of all beats, selects T-wave derived features that are within standard deviations with respect to the mean values, respectively, and generates a T-wave feature profile based on the selected T-wave derived features. If three beats occur in a predetermined time period, the derived features of three T waves are generated by the derived feature generator 113.

Since the T-wave derived features of each beat include a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change in T-wave left area, a change in T-wave right area, and other factors known to one having ordinary skill in the art, in this example, the profile generator 114 calculates mean values of factors included in the T-wave derived features of the three T waves After obtaining the mean values of the factors, the profile generator 114 compares factors included in the T-wave derived features of each beat to the corresponding mean values, respectively, to calculate standard deviations, selects T-wave derived features that are within standard deviations to generate a T-wave derived feature pattern including the selected T-wave derived features, and generates a T-wave feature profile including the T-wave derived feature pattern.

In an example, the profile generator 114 compares the T-wave derived features of each beat to predetermined threshold conditions, selects T-wave derived features that meet the predetermined threshold conditions, and generates a T-wave feature profile based on the selected T-wave derived features. If three beats occur in a predetermined time period, T-wave derived features of three T waves are generated by the derived feature generator 113.

Since T-wave derived features of each beat include a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change ($\Delta T_{left}$) in T-wave left duration, a change ($\Delta T_{right}$) in T-wave right duration, a change in T-wave amplitude, a change in T-wave area, a change in T-wave left area, a change in T-wave right area, and other factors known to one having ordinary skill in the art, in this example, the profile generator 114 compares each of the factors included in the T-wave derived features of each beat to a predetermined threshold value to determine whether the corresponding factor is greater than or less than the predetermined threshold value, and selects T-wave derived features that meet threshold conditions according to the result of the determination to thereby generate a T-wave feature profile including the selected T-wave derived features.

The prediction model generator 120 classifies the T-wave feature profile generated by the feature extractor 110 to thereby generate an AF prediction model. For example, the prediction model generator 120 compares T-wave feature profiles of an AF patient group to T-wave feature profiles of an AF non-patient group, the T-wave feature profiles generated by the feature extractor 110, and classified AF aspects according to T-wave derived feature patterns included in the T-wave feature profiles, thereby generating AF prediction models.

If AF data of the AF patient group and the AF non-patient group is inputted to the feature extractor 110, T-wave feature profiles of the AF patient group and the AF non-patient group are generated by the feature extractor 110.

The prediction model generator 120 compares the T-wave feature profiles of the AF patient group to the T-wave feature profiles of the AF non-patient group, and classifies AF aspects according to T-wave derived feature patterns included in the corresponding T-wave feature profiles, thereby generating AF prediction models.

Thereby, the AF prediction model generating apparatus 100 analyzes electrocardiogram data in a predetermined time period to extract the features of a T wave from the electrocardiogram data, and generates an AF prediction model that can be used for AF prediction, based on the T-wave features.

According to an example, the AF prediction model generating apparatus 100 includes an electrocardiogram database 130. The electrocardiogram database 130 stores electrocardiogram data of at least one AF patient and at least one AF non-patient.

That is, the electrocardiogram database 130 collects AF data of at least one AF patient and at least one AF non-patient, measured by an electrocardiogram measuring apparatus (not shown), stores the collected AF data in the electrocardiogram database 130, and creates AF prediction models based on the AF data of the AF patient group and AF non-patent group stored in the electrocardiogram database 130.

According to an example, the AF prediction model generating apparatus 100 includes a prediction model database 140. The prediction model database 140 stores AF prediction models generated by the prediction model generator 120. The AF prediction models stored in the prediction model database 140 are used for an AF prediction apparatus 200 (will be described later) to predict a future generation possibility of AF in real time.

Figure 3:
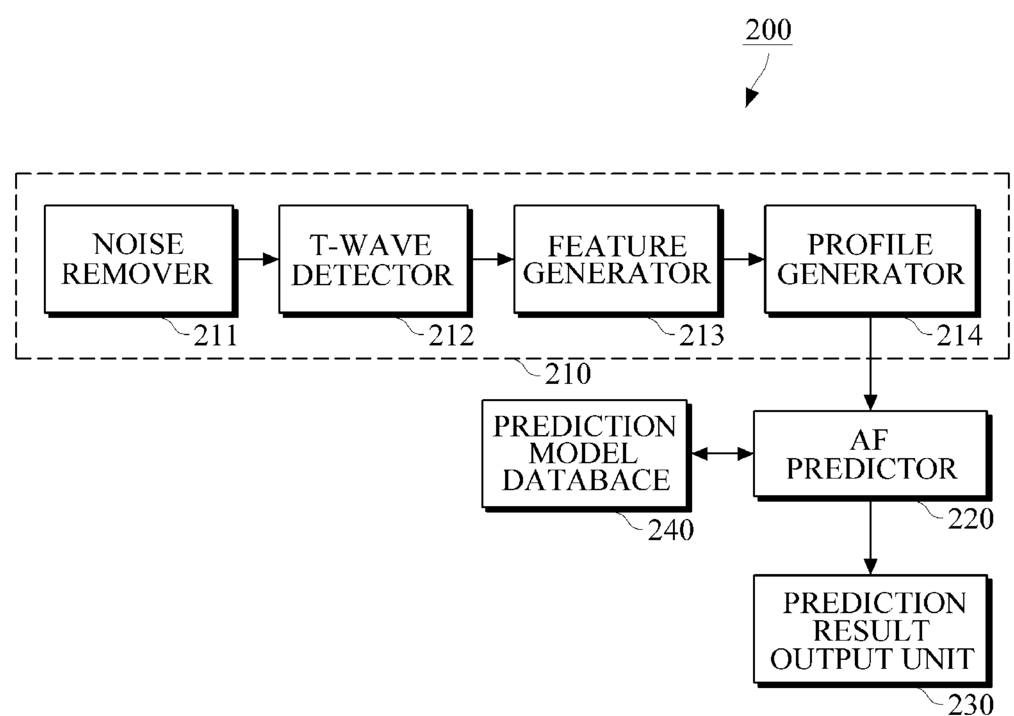
FIG. 3 is a block diagram illustrating an example of an AF prediction apparatus.

FIG. 3 is a block diagram illustrating an example of an AF prediction apparatus 200. The AF prediction apparatus 200 illustrated in the example of FIG. 3 includes a feature extractor 210, an AF predictor 220, a prediction result output unit 230, and a prediction model database 240.

The feature extractor 210 extracts T-wave features in a predetermined time period from a target's electrocardiogram data. The target's electrocardiogram data is collected in real time, and analyzes the T-wave features to thereby generate a T-wave feature profile. The AF data of a target, which is a patient that will have an operation or any other type of patient known to one having ordinary skill in the art having AF, is measured in real time by an electrocardiogram measuring apparatus (not shown). A plurality of pieces of electrocardiogram data may be measured through a plurality of measurement channels corresponding to the number of electrodes that are attached to a body.

In order to predict a possibility that AF will be generated in a target, based on T-wave information, in this example, the feature extractor 210 includes a noise remover 211, a T-wave detector 212, a derived feature generator 213, and a profile generator 214.

The noise remover 211 eliminates noise contained in a target's electrocardiogram data. The target's electrocardiogram data may include noise, baseline wandering, and other factors known to cause inaccurate measurement to the those of ordinary skill in the art. The noise remover 211 serves to eliminate these inaccurate measurement factors.

The T-wave detector 212 detects basic features of a T wave in a predetermined time period from the target's electrocardiogram data from which noise has been eliminated by the noise remover 211. Here, the predetermined time period extends from a previous time point to a current time point. A plurality of beats may be included in the predetermined time period. Accordingly, the example of the electrocardiogram data waveform as illustrated in FIG. 2 may appear several times in the predetermined time period.

Meanwhile, since electrocardiogram data is measured by an electrocardiogram measuring apparatus (not shown) and, in this example, a plurality of pieces of electrocardiogram data are measured through a plurality of measurement channels corresponding to the number of electrodes that are attached to a body, the T-wave detector 212 detects the basic features of a T wave in a predetermined time period from the measured electrocardiogram data for each channel.

Further, in this example, the T-wave basic features include, as shown in FIG. 2, one or more pieces of information, among a T-wave start location $T_{onset}$, a T-wave peak location $T_{peak}$, a T-wave termination location $T_{offset}$, a T-wave amplitude $T_{amplitude}$, a T-wave area $T_{area}$, a T-wave left area, and a T-wave right area.

The derived feature generator 213 analyzes the T-wave basic features to generate T-wave derived features for each beat. In this example, the T-wave derived features, derived from the T-wave basic features, include one or more pieces of information among a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change ($\Delta T_{left}$) in T-wave left duration, a change ($\Delta T_{right}$) in T-wave right duration, a change in T-wave amplitude, a change in T-wave area, a change in T-wave left area, and a change in T-wave right area.

The profile generator 214 generates a T-wave feature profile based on T-wave derived features for each of the beats. The T-wave feature profile, in this example, includes a T-wave derived feature pattern and is used to search for an AF prediction model upon AF prediction.

In this example, the profile generator 214 calculates mean values of T-wave derived features for all beats to generate a T-wave feature profile. If three beats occur in a predetermined time period, derived features of three T waves are generated by the derived feature generator 213 for the three beats.

The T-wave derived features for each beat may include a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change ($\Delta T_{left}$) in T-wave left duration, a change ($\Delta T_{right}$) in T-wave right duration, a change in T-wave amplitude, a change in T-wave area, a change in T-wave left area, and a change in T-wave right area, and other factors known to one having ordinary skill in the art. Accordingly, in this example, the profile generator 214 calculates mean values of the factors included in the derived features of the three T waves.

After calculating the mean values of the factors, the profile generator 214 generates a new T-wave derived feature pattern formed with factors having the mean values, and a T-wave feature profile including the new T-wave derived feature pattern.

In an example, the profile generator 214 calculates mean values of the T-wave derived features of all beats, selects T-wave derived features that are within standard deviations with respect to the mean values, respectively, and generates a T-wave feature profile based on the selected T-wave derived features. If three beats occur in a predetermined time period, T-wave derived features for three T waves are generated by the derived feature generator 213.

Since the T-wave derived features of each beat include a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change $\Delta T_{left}$ in T-wave left duration, a change $\Delta T_{right}$ in T-wave right duration, a change in T-wave amplitude, a change in T-wave area, a change in T-wave left area, a change in T-wave right area, and other factors known to one having ordinary skill in the art, the profile generator 214 calculates mean values of factors included in the derived features of the three T waves.

After calculating the mean values of the factors, the profile generator 214 calculates mean values of the T-wave derived features of all beats, compares factors included in the T-wave derived features of each beat to the corresponding mean values, respectively, to calculate standard deviations, selects T-wave derived features that are within standard deviations to generate a T-wave derived feature pattern including the selected T-wave derived features, and generates a T-wave feature profile including the T-wave derived feature pattern.

In an example, the profile generator 214 compares the T-wave derived features of each beat to predetermined threshold conditions, selects T-wave derived features that meet the predetermined threshold conditions, and generates a T-wave feature profile. If three beats occur in a predetermined time period, the T-wave derived features of three T waves are generated by the derived feature generator 213.

Since T-wave derived features for each beat include a T-wave duration ($T_{offset}-T_{onset}$), a T-wave left duration ($T_{left}=T_{peak}-T_{onset}$), a T-wave right duration ($T_{right}=T_{offset}-T_{peak}$), a change ($\Delta T$) in T-wave duration, a change ($\Delta T_{left}$) in T-wave left duration, a change ($\Delta T_{right}$) in T-wave right duration, a change in T-wave amplitude, a change in T-wave area, a change in T-wave left area, a change in T-wave right area, and other factors known to one having ordinary skill in the art, the profile generator 214 compares each of the factors included in the T-wave derived features of each beat to a predetermined threshold value to determine whether the corresponding factor is greater than or less than the predetermined threshold value, and selects T-wave derived features that meet predetermined threshold conditions according to the results of the determination to thereby generate a T-wave feature profile including the selected T-wave derived features.

Figure 4:
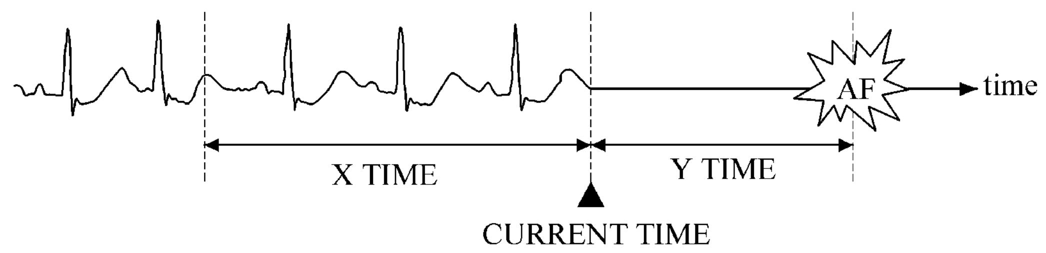
FIG. 4 is a diagram illustrating an example to explain an AF prediction that is performed by the AF prediction apparatus.

FIG. 4 is diagram illustrating an example to explain an AF prediction that is performed by the AF prediction apparatus 200. In this example, in order to predict a possibility of AF generation after a y time elapses from a current time, the AF prediction apparatus 200 detects T-wave features and T-wave derived features from a target's electrocardiogram data that is collected from a previous time point x to a current time to generate a T-wave feature profile.

The AF predictor 220 searches for a T-wave derived feature pattern according to an AF aspect corresponding to the generated T-wave feature profile with reference to pre-stored AF prediction models to predict a possibility of AF generation in the target as a result.

Since AF prediction models classify AF aspects according to T-wave derived feature patterns included in T-wave feature profiles analyzed from electrocardiogram data of an AF patient group and an AF non-patient group, in this example, the AF predictor 220 searches for an AF aspect corresponding to a target's T-wave feature profile generated by the feature extractor 210 from the AF prediction models to predict a future time point at which AF may be generated in the target as a result.

The prediction result output unit 230 outputs the predicted results about the possibility of AF generation and a future time point at which AD may be generated in the target. In an example, the prediction result output unit 230 outputs the predicted results through a liquid crystal display a light emitting diode screen of the AF prediction apparatus 200. In addition, in an example, the prediction result output unit 230 outputs the predicted results through a printer or other output devices known to one having ordinary skilled in the art that are connected to the AD prediction apparatus 200. Further, in an example, the prediction result output unit 230 outputs the predicted results through a PC, a server, a medical machine, or other network devices known to one of ordinary skill in the art that are connected to the prediction result output unit 230.

As a result, the AF prediction apparatus 200 collects electrocardiogram data of a target in real time, analyzes the electrocardiogram data of the target in a predetermined time period to extract the features of a T wave from the electrocardiogram data, and searches for an AF prediction model associated with the extracted features of the T wave to predict a possibility of future AF generation.

Further, in an example, the AF prediction apparatus 200 includes a prediction model database 240. The prediction model database 240 stores AF prediction models that classify AF aspects according to T-wave derived feature patterns included in T-wave feature profiles. In other words, in the current example, the AF prediction apparatus 200 includes the prediction model database 240 that stores the AF prediction models to be referred to when AF generation is predicted.

Figure 5:
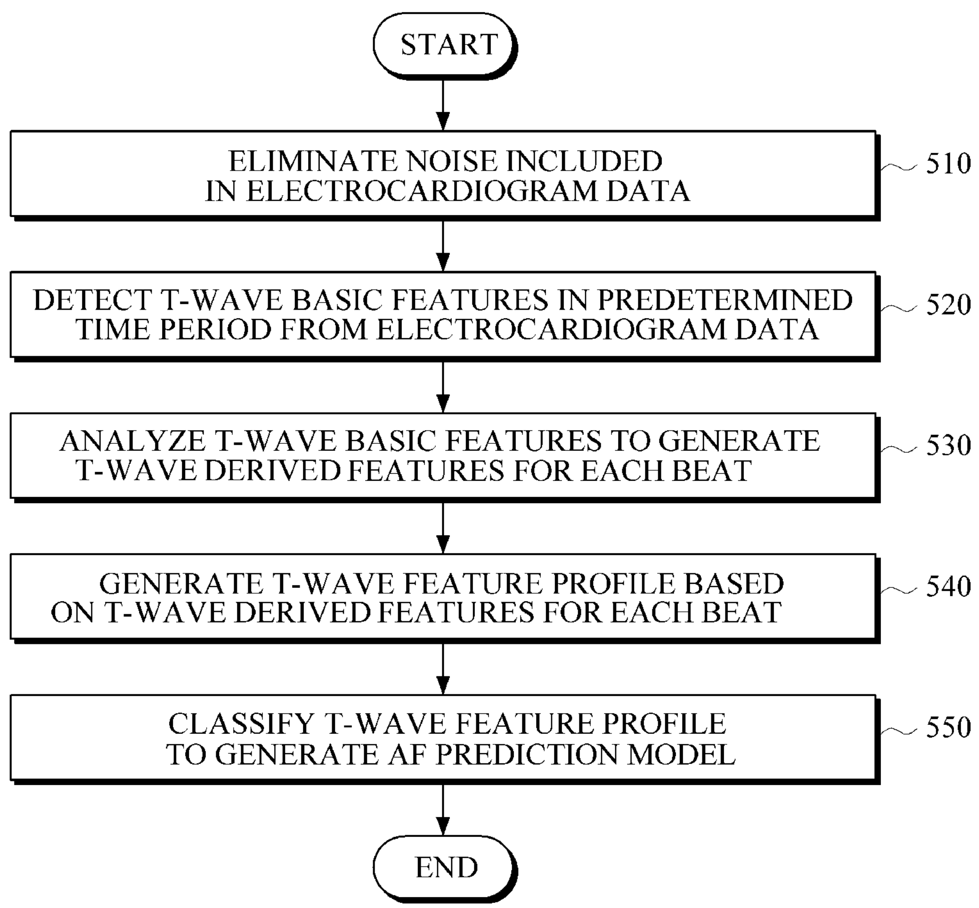
FIG. 5 is a flowchart illustrating an example of an AF prediction model generation method.

FIG. 5 is a flowchart illustrating an example of an AF prediction model generating method. Referring to FIG. 5, noise included in electrocardiogram data is eliminated (510). T-wave basic features in a predetermined time period are detected (520) from the electrocardiogram data from which the noise has been eliminated. The detected T-wave basic features are analyzed (530) to generate T-wave derived features for each beat. A T-wave feature profile based on the generated T-wave derived features is generated (540) for each beat. The generated T-wave feature profile is classified (550) to generate an AF prediction model. In this way, the AF prediction model generating apparatus 100 analyzes electrocardiogram data in a predetermined time period to extract the features of a T wave, and generates an AF prediction model based on the extracted features of the T wave.

Figure 6:
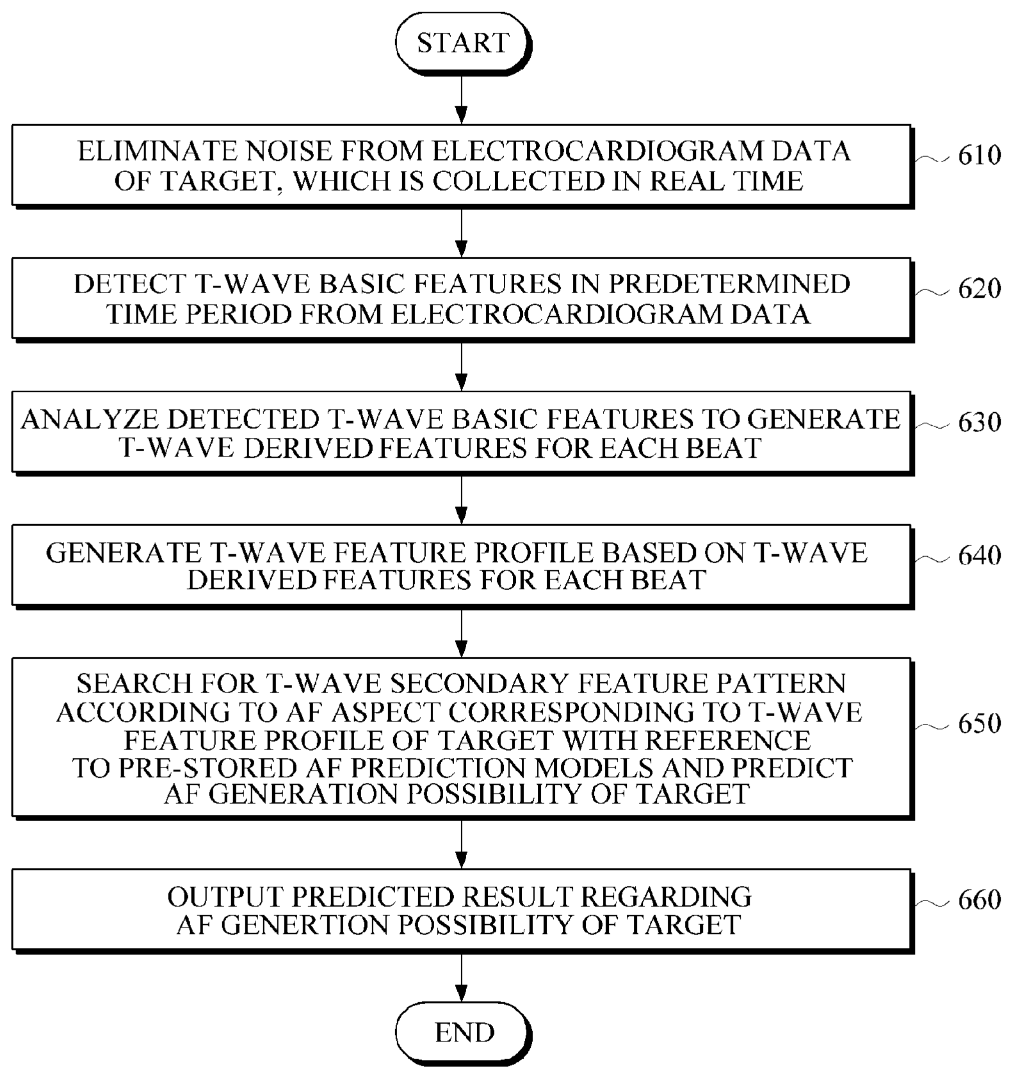
FIG. 6 is a flowchart illustrating an example of an AF generation possibility predicting method.

FIG. 6 is a flowchart illustrating an example of an AF generation possibility predicting method. Referring to the example illustrated in FIG. 6, noise from electrocardiogram data of a target, which is collected in real time, is eliminated (610). T-wave basic features in a predetermined time period are detected (620) from the electrocardiogram data from which noise has been eliminated. The detected T-wave basic features are analyzed (630) to generate T-wave derived features for each beat. A T-wave feature profile of the target is generated (640) based on the T-wave derived features for each beat. A T-wave derived feature pattern is searched for (650) according to an AF aspect corresponding to the T-wave feature profile for the target with reference to pre-stored AF prediction models. An AF generation possibility of the target is thereby predicted as a result. A result value regarding the predicted AF generation possibility of the target is outputted (660). In this way, the AF prediction apparatus 200 analyzes the electrocardiogram data of the target in a predetermined time period to extract the features of a T wave from the electrocardiogram data, and searches for an AF prediction model associated with the extracted features of the T wave, thereby predicting a future generation possibility of AF.

The units and elements described herein may be implemented using hardware components and software components, such as, but not limited to, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An atrial fibrillation (AF) prediction model generating apparatus, comprising:

a feature extractor configured to extract T-wave features in a predetermined time period from electrocardiogram data and generate a T-wave feature profile based on the extracted T-wave features; and a prediction model generator configured to classify the generated T-wave feature profile and generate an AF prediction model based on the classified feature profile for predicting a future generation possibility of AF in real time.

2. The AF prediction model generating apparatus of claim 1, wherein the feature extractor comprises a noise remover, a T-wave detector, a derived feature generator, and a profile generator, the noise remover being configured to eliminate noise in the electrocardiogram data, the T-wave detector being configured to detect T-wave basic features in the predetermined time period from the electrocardiogram data from which the noise has been eliminated, the derived feature generator being configured to analyze the detected T-wave basic features and generate T-wave derived features for beats occurring during the predetermined time period based on the analyzed T-wave basic features, the profile generator being configured to generate the T-wave feature profile based on the generated T-wave derived features for the beats occurring during the predetermined time period.

3. The AF prediction model generating apparatus of claim 2, wherein the profile generator is further configured to calculate mean values of the generated T-wave derived features for the beats occurring during the predetermined time period and generate the T-wave feature profile based on the calculated mean values.

4. The AF prediction model generating apparatus of claim 2, wherein the profile generator is further configured to calculate mean values of the generated T-wave derived features for the beats occurring during the predetermined time period, select ones of the generated T-wave derived features that are within standard deviations with respect to the calculated mean values, respectively, and generate the T-wave feature profile based on the selected ones of the generated T-wave derived features.

5. The AF prediction model generating apparatus of claim 2, wherein the profile generator is further configured to compare the generated T-wave derived features for the beats occurring during the predetermined time period to predetermined threshold conditions, select ones of the generated T-wave derived features that meet the predetermined threshold conditions, and generate the T-wave feature profile based on the selected ones of the generated T-wave derived features.

6. The AF prediction model generating apparatus of claim 2, wherein the T-wave detector is further configured to detect the T-wave basic features in the predetermined time period from the electrocardiogram data for one or more measurement channels.

7. The AF prediction model generating apparatus of claim 2, wherein the detected T-wave basic features comprise one or more first pieces of information selected from the group consisting of a T-wave start location, a T-wave peak location, a T-wave termination location, a T-wave amplitude, a T-wave area, a T-wave left area, and a T-wave right area.

8. The AF prediction model generating apparatus of claim 7, wherein the generated T-wave derived features comprise one or more second pieces of information selected from the group consisting of a T-wave duration, a T-wave left duration, a T-wave right duration, a change in the T-wave duration, a change in the T-wave left duration, a change in the T-wave right duration, a change in the T-wave amplitude, a change in the T-wave area, a change in the T-wave left area, and a change in the T-wave right area.

9. The AF prediction model generating apparatus of claim 1, wherein the prediction model generator is further configured to compare T-wave feature profiles of an AF patient group to T-wave feature profiles of an AF non-patient group, the T-wave feature profiles being generated by the feature extractor, classify AF aspects according to T-wave derived feature patterns included in the T-wave feature profiles, and generate AF prediction models based on the classified AF aspects.

10. The AF prediction model generating apparatus of claim 1, further comprising:

an electrocardiogram database configured to store electrocardiogram data of at least one AF patient and at least one AF non-patient.

11. The AF prediction model generating apparatus of claim 1, further comprising:

a prediction model database configured to store the generated AF prediction model.

12. An atrial fibrillation (AF) prediction apparatus, comprising:

a feature extractor configured to extract T-wave features in a predetermined time period from electrocardiogram data of a target that is collected in real time and generate a T-wave feature profile based on the extracted T-wave features;

an AF predictor configured to search for a T-wave derived feature pattern according to an AF aspect corresponding to the generated T-wave feature profile with reference to AF prediction models for predicting a future possibility of AF generation in the target as a result; and a prediction result output unit configured to output the predicted result.

13. The AF prediction apparatus of claim 12, wherein the feature extractor comprises a noise remover, a T-wave detector, a derived features generator, and a profile generator, the noise remover being configured to eliminate noise and baseline wandering included in the electrocardiogram data, the T-wave detector being configured to detect T-wave basic features in the predetermined time period from the electrocardiogram data from which the noise has been eliminated, the derived features generator being configured to analyze the detected T-wave basic features and generate T-wave derived features for beats occurring during the predetermined time period based on the analyzed T-wave basic features, the profile generator being configured to generate the T-wave feature profile based on the generated T-wave derived features for the beats occurring during the predetermined time period.

14. The AF prediction apparatus of claim 13, wherein the profile generator is further configured to calculate mean values of the generated T-wave derived features for the beats occurring during the predetermined time period and generate the T-wave feature profile based on the calculated mean values of the generated T-wave derived features for the beats occurring during the predetermined time period.

15. The AF prediction apparatus of claim 13, wherein the profile generator is further configured to calculate mean values of the generated T-wave derived features for the beats occurring during the predetermined time period, select ones of the generated T-wave derived features that are within standard deviations with respect to the calculated mean values, respectively, and generate the T-wave feature profile based on the selected ones of the generated T-wave derived features.

16. The AF prediction apparatus of claim 13, wherein the profile generator is further configured to compare the generated T-wave derived features for the beats occurring during the predetermined time period to predetermined threshold conditions, select ones of the generated T-wave derived features that meet the predetermined threshold conditions, and generate the T-wave feature profile based on the selected ones of the generated T-wave derived features.

17. The AF prediction apparatus of claim 13, wherein the T-wave detector is further configured to detect the T-wave basic features in the predetermined time period from the electrocardiogram data for one or more measurement channels.

18. The AF prediction apparatus of claim 13, wherein the detected T-wave basic features comprise one or more first pieces of information selected from the group consisting of a T-wave start location, a T-wave peak location, a T-wave termination location, a T-wave amplitude, a T-wave area, a T-wave left area, and a T-wave right area.

19. The AF prediction apparatus of claim 18, wherein the generated T-wave derived features comprise one or more second pieces of information selected from the group consisting of a T-wave duration, a T-wave left duration, a T-wave right duration, a change in the T-wave duration, a change in the T-wave left duration, a change in the T-wave right duration, a change in the T-wave amplitude, a change in the T-wave area, a change in the T-wave left area, and a change in the T-wave right area.

20. The AF prediction apparatus of claim 12, further comprising:

a prediction model database configured to store ones of the AF prediction models that classify AF aspects according to T-wave derived feature patterns included in T-wave feature profiles.

21. A method of generating an atrial fibrillation (AF) prediction model, the method comprising:

eliminating noise included in electrocardiogram data;

detecting T-wave basic features in a predetermined time period from the electrocardiogram data from which the noise has been eliminated;

analyzing the T-wave basic features and generating T-wave derived features for beats occurring during the predetermined time period based on the analyzed T-wave basic features;

generating a T-wave feature profile based on the generated T-wave derived features for the beats occurring during the predetermined time period; and classifying the generated T-wave feature profile and generating an AF prediction model, using a prediction model generator, based on the classified T-wave feature profile for predicting a future generation possibility of AF in real time.

22. An atrial fibrillation (AF) prediction method, the method comprising:

eliminating noise from electrocardiogram data of a target, which is collected in real time;

detecting T-wave basic features in a predetermined time period from the electrocardiogram data from which the noise has been eliminated;

analyzing the detected T-wave basic features and generating T-wave derived features for beats occurring during the predetermined time period based on the analyzed T-wave basic features;

generating a T-wave feature profile of the target based on the generated T-wave derived features for the beats occurring during the predetermined time period;

predicting a future possibility of AF generation of the target as a result, the predicting of the result comprising searching for a T-wave derived feature pattern according to an AF aspect corresponding to the generated T-wave feature profile of the target with reference to pre-stored AF prediction models which were generated using a prediction model generator; and outputting the predicted result regarding the AF generation possibility of the target.

* * * * *